(12) United States Patent
Kim et al.

(10) Patent No.: US 10,947,209 B2
(45) Date of Patent: Mar. 16, 2021

(54) METHOD FOR PREPARING 2, 5-FURANDIMETHYLCARBOXYLATE FROM HYDROXYMETHYLFURFURAL

(71) Applicants: KOREA INSTITUTE OF INDUSTRIAL TECHNOLOGY, Cheonan-si (KR); SK CHEMICALS CO., LTD., Seongnam-si (KR)

(72) Inventors: Yong Jin Kim, Yongin-si (KR); Dinesh Kumar Mishra, Cheonan-si (KR); Jin Ku Cho, Yongin-si (KR); Yong Jin Yi, Uiwang-si (KR); Han Seok Kim, Yongin-si (KR); Jong Ryang Kim, Seongnam-si (KR)

(73) Assignees: Korea Institute of Industrial Technology, Cheonan-si (KR); SK CHEMICALS CO., LTD., Seongnam-si (KR)

( * ) Notice: Subject to any disclaimer, the term of this patent is extended or adjusted under 35 U.S.C. 154(b) by 0 days.

(21) Appl. No.: 16/627,685

(22) PCT Filed: Jun. 29, 2018

(86) PCT No.: PCT/KR2018/007404
§ 371 (c)(1),
(2) Date: Dec. 30, 2019

(87) PCT Pub. No.: WO2019/004777
PCT Pub. Date: Jan. 3, 2019

(65) Prior Publication Data
US 2020/0148658 A1    May 14, 2020

(30) Foreign Application Priority Data

Jun. 30, 2017  (KR) ........................ 10-2017-0083706

(51) Int. Cl.
*C07D 307/68*    (2006.01)
(52) U.S. Cl.
CPC .................................. *C07D 307/68* (2013.01)
(58) Field of Classification Search
CPC .................................................. C07D 307/68
USPC ....................................................... 549/485
See application file for complete search history.

(56) References Cited

PUBLICATIONS

Menegazzo et al. II, "On the process, etc.," Journal of Catalysis 319, 61-70 (Year: 2014).*
Casanova, O. et al., "Biomass into chemicals: One pot-base free oxidative esterification of 5-hydroxymethyl-2-furfural into 2,5-dimethylfuroate with gold on nanoparticulated ceria", Journal of Catalysis, vol. 265, pp. 109-116 (May 28, 2009).
Gao, J. et al., "Oxidative Esterification of Methacrolein to Methyl Methacrylate over Gold Nanoparticles on Hydroxyapatite", ChemCatChem, 2017, vol. 9, pp. 1230-1241.
Gorbanev, Y. Y. et al., "Gold-Catalyzed Aerobic Oxidation of 5-Hydroxymethyl furfural in Water at Ambient Temperature", ChemSusChem, 2009, vol. 2, No. 7, pp. 672-675.
Gupta, N. K. et al., "Hydrotalcite-supported gold-nanoparticle-catalyzed highly efficient base-free aqueous oxidation of 5-hydroxymethylfurfural into 2,5-furandicarboxylic acid under atmospheric oxygen pressure", Green Chemistry, vol. 13, pp. 824-827 (Feb. 14, 2011).
Korean Office Action dated Mar. 27, 2019.
Menegazzo, F. et al., Structure-activity Relationships of Au/ZrO2 Catalysts for 5-hydroxymethylfurfural oxidative esterification: Effects of zirconia sulphation on gold dispersion, position and shape, Journal of Catalysis, 2015, vol. 326, pp. 1-8.
Radhakrishnan, R. et al., "Oxidative esterification of furfural over Au—Pd/HAP-T and Au—Ag/HAP-T bimetallic catalysts supported on mesoporous hydroxyapatite nanorods", RSC Advances, vol. 6, pp. 45907-45922 (May 3, 2016).
Taarning, E. et al., "Chemicals from Renewables: Aerobic Oxidation of Furfural and Hydroxymethylfurfural over Gold Catalysts", ChemSusChem, 2008, vol. 1, Nos. 1-2, pp. 75-78.
Zhang, Z. et al., "Recent Advances in the Catalytic Synthesis of 2,5-Furandicarboxylic Acid and Its Derivatives", ACS Catalysis, 2015, vol. 5, No. 11, pp. 6529-6544.

* cited by examiner

*Primary Examiner* — Patricia L Morris
(74) *Attorney, Agent, or Firm* — Rabin & Berdo, P.C.

(57) ABSTRACT

An embodiment of the present invention provides a method of preparing 2,5-furandimethylcarboxylate (FDMC), including preparing 2,5-furandimethylcarboxylate (FDMC) by subjecting a reaction mixture including 5-hydroxymethylfurfural (HMF), air, and an alcohol solvent to oxidative esterification in the presence of a gold (Au)-nanoparticle-supported catalyst, in which the gold (Au)-nanoparticle-supported catalyst includes a support and gold (Au) nanoparticles supported on the support.

5 Claims, 14 Drawing Sheets

METHOD FOR PREPARING 2,5-FURANDIMETHYLCARBOXYLATE FROM HYDROXYMETHYLFURFURAL

TECHNICAL FIELD

The present invention relates to a method of preparing 2,5-furandimethylcarboxylate (FDMC), and more particularly to the preparation of 2,5-furandimethylcarboxylate (FDMC) from 5-hydroxymethylfurfural (HMF) through oxidative esterification in a single vessel using a gold (Au) catalyst supported on hydroxyapatite (HAP).

BACKGROUND ART

With the establishment of industrial production systems following World War II, plastics based on various resins began to be mass-produced as consumer goods. Particularly since the late 1970s, more than 30 million tons of plastics have recently been produced and consumed worldwide, exceeding the production of steel. However, plastics, which are produced using naphtha resulting from refining petroleum, are problematic because depletion of petroleum resources and carbon dioxide emissions occur. Furthermore, plastics are used as the main material for disposable products and are thus discarded in large amounts immediately after use, and do not decay for a long time, making landfill disposal thereof difficult. When plastics are incinerated, carcinogens including dioxins are released to the atmosphere, causing environmental problems. Hence, research into materials capable of replacing plastics is continuing.

As materials capable of replacing plastics, scientists are working on the development of bioplastics using plant starch or cellulose. In particular, a plastic produced based on 2,5-furandicarboxylic acid (FDCA), among bioplastic materials, is receiving attention.

FDCA is typically prepared from 5-hydroxymethylfurfural (HMF), raw materials for which are difficult to obtain, through oxidation using an explosive oxidizing agent such as pure oxygen in the presence of a noble metal catalyst. However, it is difficult to prepare FDCA on a large scale because HMF is hard to mass-produce due to the difficulty in obtaining raw materials, and because of the high explosivity at the time of an oxidation reaction using pure oxygen as an oxidizing agent.

In addition, FDCA has the problem of low solubility in industrial solvents.

With the goal of overcoming the above problem, FDCA may be replaced with an ester corresponding thereto, i.e. FDMC, which is readily soluble in the most common solvents. Hence, the process of converting HMF into FDMC may have an influence on the polymer industry.

However, in the process of preparing FDMC by adding a base to HMF in a catalytic reaction, the use of the base may increase the FDMC yield, but processing costs are also increased, which is undesirable.

DISCLOSURE

Technical Problem

Accordingly, an objective of the present invention is to provide a method of effectively preparing 2,5-furandimethylcarboxylate (FDMC) in order to solve the problem of low solubility of 2,5-furandicarboxylic acid (FDCA), a raw material for PEF, which is a polymer capable of replacing PET of plastics made from petroleum resources.

More specifically, plastics that cause the depletion of petroleum resources and have to be incinerated due to the difficulty in landfilling because they do not decay for a long time incur environmental problems by releasing carcinogens including dioxins, and carbon dioxide, which causes global warming, to the atmosphere upon incineration. With the aim of preventing these problems, the present invention intends to provide a method of efficiently preparing FDMC capable of overcoming the problem of low solubility of FDCA in industrial solvents, in the production of 2,5-furandicarboxylic acid (FDCA), which may be applied to the environmentally friendly biomaterial field and is an important raw material of PEF, which is a polymer capable of replacing PET.

The objectives to be achieved by the present invention are not limited to the foregoing, and additional objectives, which are not mentioned herein, will be readily understood by those skilled in the art from the following description.

Technical Solution

In order to accomplish the above objectives, an embodiment of the present invention provides a method of preparing 2,5-furandimethylcarboxylate (FDMC), including preparing 2,5-furandimethylcarboxylate (FDMC) by subjecting a reaction mixture comprising 5-hydroxymethylfurfural (HMF), air and an alcohol solvent to oxidative esterification in the presence of a gold (Au)-nanoparticle-supported catalyst, in which the gold (Au)-nanoparticle-supported catalyst includes a support and gold (Au) nanoparticles supported on the support.

In an embodiment of the present invention, the support may include hydroxyapatite (HAP).

In an embodiment of the present invention, the amount of the gold (Au) nanoparticles may be 0.5 wt % to 10 wt % based on 100 wt % of the gold-nanoparticle-supported catalyst.

In an embodiment of the present invention, the amount of the gold-nanoparticle-supported catalyst may be 0.5 mol to 2 mol, and preferably 0.7 mol to 1.5 mol, based on 100 mol of the hydroxymethylfurfural (HMF).

In an embodiment of the present invention, the alcohol solvent may include methanol.

In an embodiment of the present invention, the oxidative esterification may be carried out at a temperature of 110 to 150° C., and preferably 125 to 135° C., for 3 hr to 12 hr, and preferably 5 to 7 hr.

In an embodiment of the present invention, the oxidative esterification may be carried out at an air pressure of 1.7 to 3.1 MPa, and preferably 2.0 to 2.8 MPa.

In addition, another embodiment of the present invention provides a 2,5-furandimethylcarboxylate (FDMC) compound prepared by the above method of preparing FDMC.

Advantageous Effects

According to embodiments of the present invention, 2,5-furandimethylcarboxylate (FDMC) is simply produced through a safe process without the use of an explosive oxidizing agent (pure oxygen), unlike conventional methods of preparing 2,5-furandimethylcarboxylate (FDMC).

Furthermore the preparation of FDMC through preparing FDCA and then performing esterification thereof with an alcohol is a two-step process, but the present invention is effective in directly preparing FDMC from HMF through oxidative esterification in a single step.

According to the present invention, air and an alcohol are used as a reactant and a solvent, thus exhibiting improved safety and convenience compared to when conventional solvents are used.

Also, although the conventional preparation of 2,5-furandicarboxylic acid (FDCA) is problematic in that 2,5-furandicarboxylic acid (FDCA) has low solubility in an industrial solvent, the present invention is capable of effectively solving the problem of low solubility by preparing 2,5-furandimethylcarboxylate (FDMC).

According to the present invention, 2,5-furandimethylcarboxylate (FDMC) can be effectively prepared at high selectivity and high yield using an HAP support, rather than other supports, through reaction in a single vessel under high pressure in the presence of an Au/HAP catalyst.

The effects of the present invention are not limited to the foregoing, and should be understood to include all effects that can be reasonably anticipated from the following description.

BEST MODE

Figure 1:
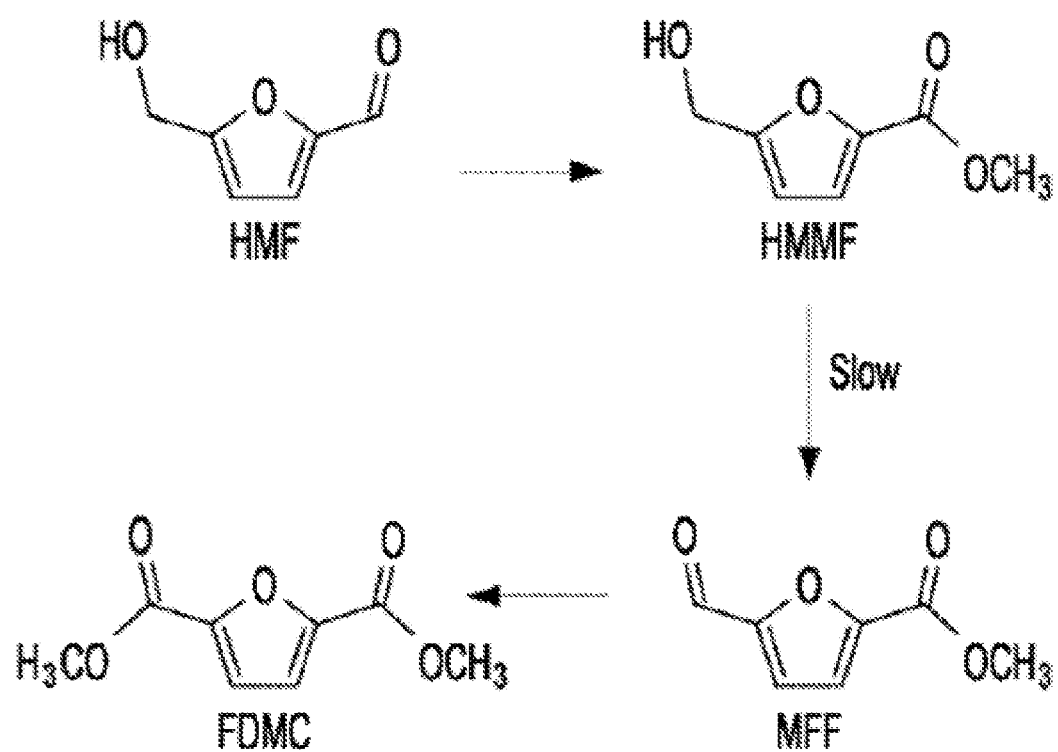
FIG. 1 shows a process of preparing 2,5-furandimethylcarboxylate (FDMC)

Hereinafter, the present invention will be described with reference to the accompanying drawings. The present invention may, however, be embodied in many different forms and is not to be construed as being limited to the exemplary embodiments set forth herein. For clarification of the invention, portions not related to the description in the drawings have been omitted. Like reference numerals designate like parts throughout the specification.

Throughout the specification, when a part is referred to as being "connected (linked, contacted, coupled)" with another part, this includes not only "directly connected" but also "indirectly connected" with a further member therebetween. Also, when a part is referred to as "comprising" or "including" any element, it means that it can include other elements, rather than necessarily excluding such other elements, unless specifically stated otherwise.

The terminology used herein is for the purpose of describing particular embodiments only and is not intended to be limiting. As used herein, the singular forms are intended to include the plural forms as well, unless the context clearly indicates otherwise. It will be further understood that the terms "comprise", "include", "have", etc. when used in this specification specify the presence of stated features, integers, steps, operations, elements, components, and/or combinations thereof, but do not preclude the presence or addition of one or more other features, integers, steps, operations, elements, components, and/or combinations thereof.

Used in the present invention, a catalyst is a substance that is added to a chemical reaction to accelerate a thermodynamically possible chemical reaction while the catalyst itself is not changed, and the catalyst is classified into, depending on the phase of a reaction system, a homogeneous catalyst, a heterogeneous catalyst, and an enzymatic catalyst. Here, the critical factors affecting catalyst properties are activity, selectivity and lifetime.

An embodiment of the present invention pertains to a method of preparing 2,5-furandimethylcarboxylate (FDMC).

The method of preparing 2,5-furandimethylcarboxylate (FDMC) according to an embodiment of the present invention includes preparing 2,5-furandimethylcarboxylate (FDMC) by subjecting a reaction mixture comprising 5-hydroxymethylfurfural (HMF), air and an alcohol solvent to oxidative esterification in the presence of a gold (Au)-nanoparticle-supported catalyst, in which the gold (Au)-nanoparticle-supported catalyst includes a support and gold (Au) nanoparticles supported on the support.

The gold (Au)-nanoparticle-supported catalyst may include a support and gold (Au) nanoparticles supported on the support.

For example, the support may include hydroxyapatite (HAP).

In the preparation of FDMC, when hydroxyapatite (HAP) is used as the support on which gold (Au) nanoparticles are supported, the FDMC yield and selectivity may increase compared to when other kinds of support are used.

For example, the production of the gold (Au)-nanoparticle-supported catalyst may include preparing a mixture by mixing a support and urea, preparing a solid product by heating the mixture, and preparing a gold (Au)-nanoparticle-supported catalyst by heat-treating the solid product.

Also, the amount of the gold (Au) nanoparticles may be 0.5 wt % to 10 wt % based on 100 wt % of the supported catalyst.

If the amount of the gold (Au) nanoparticles is less than 0.5 wt % based on 100 wt % of the supported catalyst, it is difficult to exhibit the function of the catalyst, and thus conversion becomes almost impossible and, if conversion occurs, the conversion rate is remarkably low. On the other hand, if the amount of the gold (Au) nanoparticles exceeds 10 wt % based on 100 wt % of the supported catalyst, economic benefits may be negated, and the yield may decrease, which is undesirable.

The alcohol solvent may be methanol.

Based on 100 mol of the hydroxymethylfurfural (HMF), the amount of the gold-nanoparticle-supported catalyst is 0.5 mol to 2 mol, and preferably 0.7 mol to 1.5 mol. If the gold content of the supported catalyst relative to the hydroxymethylfurfural (HMF) is less than 0.5 mol, it is difficult to exhibit the function of the catalyst, and thus conversion becomes almost impossible and, if conversion occurs, the conversion rate is remarkably low. On the other hand, if the gold content thereof exceeds 2 mol, economic benefits may be negated, and the yield may decrease, which is undesirable.

When the reactant mixture is subjected to oxidative esterification in the presence of the gold (Au)-nanoparticle-supported catalyst, FDMC may be ultimately obtained.

Here, the oxidative esterification is carried out at a temperature of 110 to 150° C., and preferably 125 to 135° C., for 3 hr to 12 hr, and preferably 5 to 7 hr.

Furthermore, the oxidative esterification may be carried out at an air pressure of 1.7 to 3.1 MPa, and preferably 2.0 to 2.8 MPa.

If the air pressure is less than 1.7 MPa, the number of collisions between the catalyst and the air may decrease and thus the mass transfer rate to reach reaction active sites is low. On the other hand, if the air pressure exceeds 3.1 MPa, the reaction rate may increase and the pressure applied to the reaction vessel may become excessively large, thus causing a problem of stability, which is undesirable.

Furthermore, if the reaction temperature is excessively low or the reaction time is excessively short, the reaction activity is low and the reaction time or contact time may increase, undesirably lowering the yield of the catalyst. On the other hand, if the reaction temperature is excessively high or the reaction time is excessively long, the generation of byproducts may increase and the internal pressure of the reactor may become excessively high, thus causing a problem of stability, which is undesirable.

Below, the reaction in the method of preparing 2,5-furandimethylcarboxylate (FDMC) according to an embodiment of the present invention is described in detail.

With reference to FIG. 1, the method of preparing 2,5-furandimethylcarboxylate (FDMC) of Chemical Formula 1 below according to an embodiment of the present invention includes subjecting hydroxymethylfurfural (HMF) and an alcohol to oxidative esterification in air in the presence of a catalyst in which gold (Au) nanoparticles are supported on hydroxyapatite (HAP), thus obtaining HMMF, which is then prepared into MFF, resulting in 2,5-furandimethylcarboxylate (FDMC).

[Chemical Formula1]

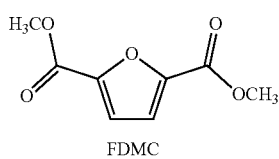

FDMC

A better understanding of the present invention will be given through the following preparation examples and test examples. However, these preparation examples and test examples are set forth to more specifically explain the construction and effects of the present invention, but are not to be construed as limiting the scope of the present invention.

MODE FOR INVENTION

The materials used in the present invention were synthesized or purchased as follows.

Tetrachloroauric(III) acid trihydrate ($HAuCl_4 \cdot 3H_2O$), ruthenium(III) chloride hydrate ($RuCl_3 \cdot xH_2O$), and dichlorobis(benzonitrile)palladium(II) [$PdCl_2(PhCN)_2$] were purchased from Sigma-Aldrich.

To prepare $MnCo_2O_4$ spinel materials, commercially available cobalt(II) acetate tetrahydrate ($CH_3COO)_2Co \cdot 4H_2O$, manganese(II) acetate tetrahydrate ($CH_3COO)_2Mn \cdot 4H_2O$, ammonium sulfate ($NH_4)_2SO_4$ and ammonium bicarbonate ($NH_4HCO_3$) were purchased from Sigma-Aldrich.

To prepare $MgAl_2O_4$ powder, magnesium nitrate hexahydrate [$Mg(NO_3)_2 \cdot 6H_2O$] was purchased from Alfa Aesar, and aluminum nitrate nonahydrate [$Al(NO_3)_3 \cdot 9H_2O$] and citric acid [$HOC(COOH)(CH_2COOH)_2$] were purchased from Sigma-Aldrich.

Cerium(III) nitrate hexahydrate [$Ce(NO_3)_3 \cdot 6H_2O$] and ammonia ($NH_3$) solution (28 to 30%) were purchased from Sigma-Aldrich and Samchun Pure Chemical, respectively.

5-hydroxymethyl-2-furfural (HMF) and 2,5-furandicarboxylate (FDMC) were purchased from Shanghai Research Institute of Chemical Industry Testing Centre and used for standard calibration. 5-hydroxymethyl methyl furoate (HMMF) was synthesized.

Urea ($NH_2CONH_2$), serving as a precipitating agent, was purchased from Daejung Chemicals & Metals. Solvents such as methanol, ethanol and acetone were purchased from Samchun Pure Chemical. Also, deionized water was used for the preparation of the catalyst.

HAP, $ZrO_2$, and $TiO_2$

Hydroxyapatite (HAP-nanopowder, <200 nm particle size, =97%, synthesized), zirconium(IV) oxide ($ZrO_2$-powder, 5 μm, 99% metal basis) and titanium(IV) oxide ($TiO_2$-nanopowder, 21 nm particle size, =99.5% metal basis) were purchased from Sigma-Aldrich and dried overnight at 80° C. in a vacuum before use.

$CeO_2$

For synthesis of $CeO_2$ having a predetermined size, a solution of 25.0 g of cerium(III) nitrate hexahydrate [$Ce(NO_3)_3 \cdot 6H_2O$] in 200 ml of deionized water heated to 70° C. was added dropwise with a 25 wt % ammonia solution to adjust the pH thereof to 9, and the resulting mixture was reacted for 1 hr. Thereafter, the solution was filtered, and the recovered solid was dried overnight at 100° C. and calcined at 550° C. for 6 hr. The $CeO_2$-supported gold nanocatalyst was prepared in accordance with the same standard homogeneous deposition-precipitation (HDP) method as was described for Au/HAP, and was represented as Au/$CeO_2$ (Au content: 1.0 wt %).

$MgAl_2O_4$

Stoichiometric amounts of magnesium nitrate hexahydrate and nitrate aluminum nonahydrate (1:2 mol ratio) were dissolved in distilled water and added with a stoichiometric amount of citric acid. After thorough mixing, a homogeneous solution was obtained. The solution was slowly evaporated until a highly viscous colloid was formed, and was then heated at 120 to 140° C. for 24 hr to obtain a dry gel. Finally, after pulverization into a fine powder, the dry gel precursor was fired at 600° C. to afford $MgAl_2O_4$ powder. The $MgAl_2O_4$-supported gold nanocatalyst was represented as ($Au/MgAl_2O_4$) (Au content: 2.1 wt %).

$MnCo_2O_4$

In typical synthesis of fine spherical $MnCo_2O_4$ spinel, $(CH_3COO)_2Mn.4H_2O$ (32.6 mmol) and $(CH_3COO)_2Co.4H_2O$ (65.3 mmol) (Mn:Co=1:2) were dissolved in water and homogenized with vigorous stirring for 30 min. Separately, ammonium sulfate (50 g) was dissolved in water (400 ml). These solutions were slowly mixed and stirred for 4 hr. Subsequently, an ammonium bicarbonate aqueous solution (~50 g) was slowly added to the above mixture and stirred for 6 hr. The resulting pale pink precipitate was collected by filtration, washed with distilled water and anhydrous ethanol, and dried at 60° C. for 12 hr. The carbonate precursor thus obtained was calcined in a furnace at 425° C. (2° C. $min^{-1}$) in air for 8 hr, allowed to stand for an additional 8 hr, and then naturally cooled to room temperature. The $MnCo_2O_4$-supported gold nanocatalyst was prepared through the same HDP method and represented as ($Au/MnCo_2O_4$) (Au content: 2.1 wt %).

PREPARATION EXAMPLES

Preparation of Supported Catalyst

Preparation Example 1

1.0 wt % Au Nanoparticles/HAP-Supported Catalyst

A standard method, a homogeneous deposition-precipitation (HDP) method using urea, was used to deposit gold nanoparticles on a support (s). 3.0 g of an HAP support was added to 20 ml of an aqueous solution of $HAuCl_4$ (0.064 g, 0.161 mmol) and urea (0.97 g, 16.2 mmol) serving as a precipitating agent (urea/Au=100, mol ratio). Then, the resulting suspension was heated to 90° C. and stirred for 4 hr. Then, the suspension was centrifuged at 3,000 rpm for 30 min and washed several times with deionized water. Then, the recovered solid product was dried overnight at 100° C. in a vacuum. The fine powder of the recovered solid product was calcined at 300° C. for 4 hr. Thereafter, purple Au/HAP (Au content: 1.0 wt %) was obtained.

Preparation Example 2

1.5 wt % Au Nanoparticles/HAP-Supported Catalyst 1.5% Au/HAP, as an Au-nanoparticle-supported catalyst, was prepared in the same manner as in Preparation Example 1, with the exception that a gold nanoparticle precursor was used so that 1.5 wt % gold nanoparticles were deposited on the HAP support, in lieu of using the gold nanoparticle precursor so that 1.0 wt % gold nanoparticles were deposited on the HAP support.

Comparative Preparation Example 1

2.0 wt % Pd Nanoparticles/HAP-Supported Catalyst

HAP (2.0 g) and an acetone aqueous solution of $PdCl_2(PhCN)_2$ (0.1478 g, Pd content: 2.0 wt %, 0.385 mmol/g) were stirred at room temperature for 3 hr. Then, the resulting slurry was filtered, washed with acetone, and dried in a vacuum, thus obtaining 2.0 wt % Pd/HAP.

Comparative Preparation Example 2

2.0 wt % Ru Nanoparticles/HAP-Supported Catalyst 1.0 g of HAP and an aqueous solution of $RuCl_3.xH_2O$ (0.046 g, Ru content: 2.0 wt %, 0.203 mmol/g) were stirred at room temperature for 24 hr. Then, the resulting slurry was filtered, washed with deionized water, and dried overnight at 100° C., thus obtaining 2.0 wt % Ru/HAP.

Comparative Preparation Example 3

1.0 wt % Au Nanoparticles/$ZrO_2$-Supported Catalyst 1.0% Au/$ZrO_2$, as an Au nanoparticle-supported catalyst, was prepared in the same manner as in Preparation Example 1, with the exception that a $ZrO_2$ support was used in lieu of the HAP support.

Comparative Preparation Example 4

1.0 wt % Au Nanoparticles/$TiO_2$-Supported Catalyst 1.0% Au/$TiO_2$, as an Au nanoparticle-supported catalyst, was prepared in the same manner as in Preparation Example 1, with the exception that a $TiO_2$ support was used in lieu of the HAP support.

Comparative Preparation Example 5

1.0 wt % Au Nanoparticles/$CeO_2$-Supported Catalyst 1.0% Au/$CeO_2$, as an Au nanoparticle-supported catalyst, was prepared in the same manner as in Preparation Example 1, with the exception that a $CeO_2$ support was used in lieu of the HAP support.

Comparative Preparation Example 6

2.1 wt % Au Nanoparticles/$MgAl_2O_4$-Supported Catalyst 2.1% Au/$MgAl_2O_4$, as an Au nanoparticle-supported catalyst, was prepared in the same manner as in Preparation Example 1, with the exception that a $MgAl_2O_4$ support was used in lieu of the HAP support, and an aqueous solution of $HAuCl_4$ (0.134 g, 0.34 mmol) and urea (2.04 g, 34.02 mmol) was used in lieu of the aqueous solution of $HAuCl_4$ (0.064 g, 0.161 mmol) and urea (0.97 g, 16.2 mmol).

Comparative Preparation Example 7

2.1 wt % Au Nanoparticles/$MnCo_2O_4$-Supported Catalyst 2.1% Au/$MnCo_2O_4$, as an Au nanoparticle-supported catalyst, was prepared in the same manner as in Preparation Example 1, with the exception that a $MnCo_2O_4$ support was used in lieu of the HAP support, and an aqueous solution of $HAuCl_4$ (0.134 g, 0.34 mmol) and urea (2.04 g, 34.02 mmol)

was used in lieu of the aqueous solution of HAuCl$_4$ (0.064 g, 0.161 mmol) and urea (0.97 g, 16.2 mmol).

Comparative Preparation Example 8

HAP Support

An HAP support was used without change.

EXAMPLES

Preparation of FDMC

Respective FDMCs were prepared under test conditions of Examples and Comparative Examples of Table 1 below, and the detailed preparation method thereof was described below.

Example 1

With reference to Table 1, the preparation of FDMC from HMF was carried out using a 100 ml high-pressure stainless steel reactor equipped with a magnetic stirrer and an electric heater.

0.2513 g (2 mmol) of HMF, CH$_3$OH (20 ml), and the 1.0% Au/HAP catalyst of Preparation Example 1 were loaded in the reactor so that the HMF/Au mol ratio was 100, after which the reactor was purged with air at 0.5 MPa, and air was evacuated from the reaction mixture three times. Subsequently, the reactor was pressurized to an air pressure of 2.4 MPa and heated to 130° C. with stirring at 650 rpm, and the reaction temperature was maintained at 130° C. for a reaction time of 6 hr, and the reaction air pressure, which is the final pressure (P$_{air}$) of air entering the reactor, was maintained at 2.4 MPa using a gas reservoir equipped with a back-pressure regulator and a pressure transducer, thereby preparing FDMC. After termination of the reaction, the resulting mixture was cooled at room temperature and added with a predetermined amount of CH$_3$OH. The solid catalyst and product were separated through a filtration process.

The remaining filtrate was subjected to high-performance liquid chromatography (HPLC) to thus quantitatively analyze FDMC using a high-performance liquid chromatographer (Agilent Technologies 1200 series, Bio-Rad Aminex HPX-87 H pre-packed column, and UV-detector). H$_2$SO$_4$ (0.0005 M) in water was used as a mobile phase. The yields of FDMC and HMMF were calculated based on the HMF conversion rate and confirmed through calibration of standard product and reactant solutions.

Example 2

FDMC was prepared in the same manner as in Example 1, with the exception that the reaction temperature was maintained at 110° C., rather than 130° C.

Example 3

FDMC was prepared in the same manner as in Example 1, with the exception that the reaction temperature was maintained at 150° C., rather than 130° C.

Example 4

FDMC was prepared in the same manner as in Example 1, with the exception that the reaction air pressure was maintained at 1.7 MPa, rather than 2.4 MPa.

Example 5

FDMC was prepared in the same manner as in Example 1, with the exception that the reaction air pressure was maintained at 3.1 MPa, rather than 2.4 MPa.

Example 6

FDMC was prepared in the same manner as in Example 1, with the exception that the reaction temperature was maintained at 120° C., rather than 130° C.

Example 7

FDMC was prepared in the same manner as in Example 6, with the exception that the 1.0% Au/HAP catalyst of Preparation Example 1 was loaded so that the HMF/Au mol ratio was 93.4, rather than 100.

Example 8

FDMC was prepared in the same manner as in Example 6, with the exception that the 1.0% Au/HAP catalyst of Preparation Example 1 was loaded so that the HMF/Au mol ratio was 62.5, rather than 100.

Example 9

FDMC was prepared in the same manner as in Example 6, with the exception that the 1.5% Au/HAP catalyst of Preparation Example 2 was loaded so that the HMF/Au mol ratio was 93.4, in lieu of loading the 1.0% Au/HAP catalyst of Preparation Example 1 so that the HMF/Au mol ratio was 100, and oxygen pressure (P$_{O2}$) was maintained at 2.4 MPa during the reaction through injection of oxygen into the reactor, in lieu of maintaining the air pressure (P$_{air}$) at 2.4 MPa during the reaction through injection of air into the reactor.

Comparative Example 1

FDMC was prepared in the same manner as in Example 1, with the exception that the catalyst of Comparative Preparation Example 1 was used as the supported catalyst, in lieu of the catalyst of Preparation Example 1.

Comparative Example 2

FDMC was prepared in the same manner as in Example 1, with the exception that the catalyst of Comparative Preparation Example 2 was used as the supported catalyst, in lieu of the catalyst of Preparation Example 1.

Comparative Example 3

FDMC was prepared in the same manner as in Example 1, with the exception that the catalyst of Comparative Preparation Example 3 was used as the supported catalyst, in lieu of the catalyst of Preparation Example 1.

Comparative Example 4

FDMC was prepared in the same manner as in Example 1, with the exception that the supported catalyst of Comparative Preparation Example 4 was used as the supported catalyst, in lieu of the supported catalyst of Preparation Example 1.

Comparative Example 5

FDMC was prepared in the same manner as in Example 1, with the exception that the supported catalyst of Comparative Preparation Example 5 was used as the supported catalyst, in lieu of the supported catalyst of Preparation Example 1.

Comparative Example 6

FDMC was prepared in the same manner as in Example 1, with the exception that the supported catalyst of Comparative Preparation Example 6 was used as the supported catalyst, in lieu of the supported catalyst of Preparation Example 1, and the catalyst of Comparative Preparation Example 6 was loaded so that the HMF/Au mol ratio was 93.4, in lieu of loading the catalyst of Preparation Example 1 so that the HMF/Au mol ratio was 100.

Comparative Example 7

FDMC was prepared in the same manner as in Example 1, with the exception that the supported catalyst of Comparative Preparation Example 7 was used as the supported catalyst, in lieu of the supported catalyst of Preparation Example 1, and the catalyst of Comparative Preparation Example 7 was loaded so that the HMF/Au mol ratio was 93.4, in lieu of loading the catalyst of Preparation Example 1 so that the HMF/Au mol ratio was 100.

Comparative Example 8

FDMC was prepared in the same manner as in Example 1, with the exception that the supported catalyst of Comparative Preparation Example 8 was used as the supported catalyst, in lieu of the supported catalyst of Preparation Example 1.

TABLE 1

| | Catalyst | HMF (g) | $CH_3OH$ (ml) | Reaction time (hr) | Reaction Temp. (° C.) | Reaction pressure (MPa) | | Stirring (rpm) | HMF/Metal (mol/mol) |
|---|---|---|---|---|---|---|---|---|---|
| | | | | | | $P_{air}$ | $P_{O_2}$ | | |
| Example 1 | Au/HAP | 0.2513 | 20 | 6 | 130 | 2.4 | 0 | 650 | 100 |
| Example 2 | Au/HAP | 0.2513 | 20 | 6 | 110 | 2.4 | 0 | 650 | 100 |
| Example 3 | Au/HAP | 0.2513 | 20 | 6 | 150 | 2.4 | 0 | 650 | 100 |
| Example 4 | Au/HAP | 0.2513 | 20 | 6 | 130 | 1.7 | 0 | 650 | 100 |
| Example 5 | Au/HAP | 0.2513 | 20 | 6 | 130 | 3.1 | 0 | 650 | 100 |
| Example 6 | Au/HAP | 0.2513 | 20 | 6 | 120 | 2.4 | 0 | 650 | 100 |
| Example 7 | Au/HAP | 0.2513 | 20 | 6 | 120 | 2.4 | 0 | 650 | 93.4 |
| Example 8 | Au/HAP | 0.2513 | 20 | 6 | 120 | 2.4 | 0 | 650 | 62.5 |
| Example 9 | Au/HAP | 0.2513 | 20 | 6 | 120 | 0 | 2.4 | 650 | 93.4 |
| Comparative Example 1 | Pd/HAP | 0.2513 | 20 | 6 | 130 | 2.4 | 0 | 650 | 100 |
| Comparative Example 2 | Ru/HAP | 0.2513 | 20 | 6 | 130 | 2.4 | 0 | 650 | 100 |
| Comparative Example 3 | $Au/ZrO_2$ | 0.2513 | 20 | 6 | 130 | 2.4 | 0 | 650 | 100 |
| Comparative Example 4 | $Au/TiO_2$ | 0.2513 | 20 | 6 | 130 | 2.4 | 0 | 650 | 100 |
| Comparative Example 5 | $Au/CeO_2$ | 0.2513 | 20 | 6 | 130 | 2.4 | 0 | 650 | 100 |
| Comparative Example 6 | $Au/MgAl_2O_4$ | 0.2513 | 20 | 6 | 130 | 2.4 | 0 | 650 | 93.4 |
| Comparative Example 7 | $Au/MnCo_2O_4$ | 0.2513 | 20 | 6 | 130 | 2.4 | 0 | 650 | 93.4 |
| Comparative Example 8 | HAP | 0.2513 | 20 | 6 | 130 | 2.4 | 0 | 650 | — |

Test Examples

Analysis of Nanoparticle-Supported Catalyst

The physical and structural properties of the supported catalysts of Preparation Example 1 and Comparative Preparation Examples 3 to 5 were evaluated through various techniques. The results are shown in Table 2 below.

The wt % of gold nanoparticles adsorbed to the support was measured through inductively coupled plasma atomic emission spectrometry (ICP-AES), and the surface area, pore volume, and average pore diameter were measured through $N_2$-physisorption (adsorption-desorption), and the average particle size of the gold nanoparticles was measured through TEM analysis.

There was no significant difference between the surface area of the support and the surface area of the gold nanocatalyst corresponding thereto. This is deemed to be due to the low loading rate (~1.0 wt %) of Au. Among a variety of Au nanocatalysts, the surface area of the Au/HAP nanocatalyst of Preparation Example 1 was actually smaller than the surface area of $Au/TiO_2$ of Comparative Preparation Example 4 and the surface area of the $Au/CeO_2$ nanocatalyst of Comparative Preparation Example 5.

However, the average pore diameter of Au/HAP was 46.1 nm, which is evaluated to be the highest. An increase in the average pore diameter is analyzed to be due to the compatibility of the smallest Au nanoparticles having a particle size (2.0 to 4.0 nm) deposited on the surface of the HAP.

TABLE 2

| | Support | Amount of gold nanoparticles (wt %) Amount used | Amount supported | Surface area ($m^2/g$) | Pore volume ($cm^3/g$) | Average pore diameter (nm) | Gold nanoparticle size distribution (nm) |
|---|---|---|---|---|---|---|---|
| Preparation Example 1 | HAP | 1.0 | 0.95 | 21.3 | 0.245 | 46.1 | 2.0-4.0 |
| Comparative Preparation Example 3 | $ZrO_2$ | 1.0 | 1.05 | 5.5 | 0.031 | 22.5 | 3.0-5.0 |
| Comparative Preparation Example 4 | $TiO_2$ | 1.0 | 0.94 | 51.8 | 0.058 | 4.5 | 3.0-6.0 |
| Comparative Preparation Example 5 | $CeO_2$ | 1.0 | 1.0 | 48.8 | 0.330 | 27.2 | 3.0-5.0 |
| HAP | | — | — | >9.4 | — | — | — |
| $ZrO_2$ | | — | — | 5.4 | 0.006 | 4.4 | — |
| $CeO_2$ | | — | — | 49.1 | 0.320 | 26.4 | — |

Figure 2:
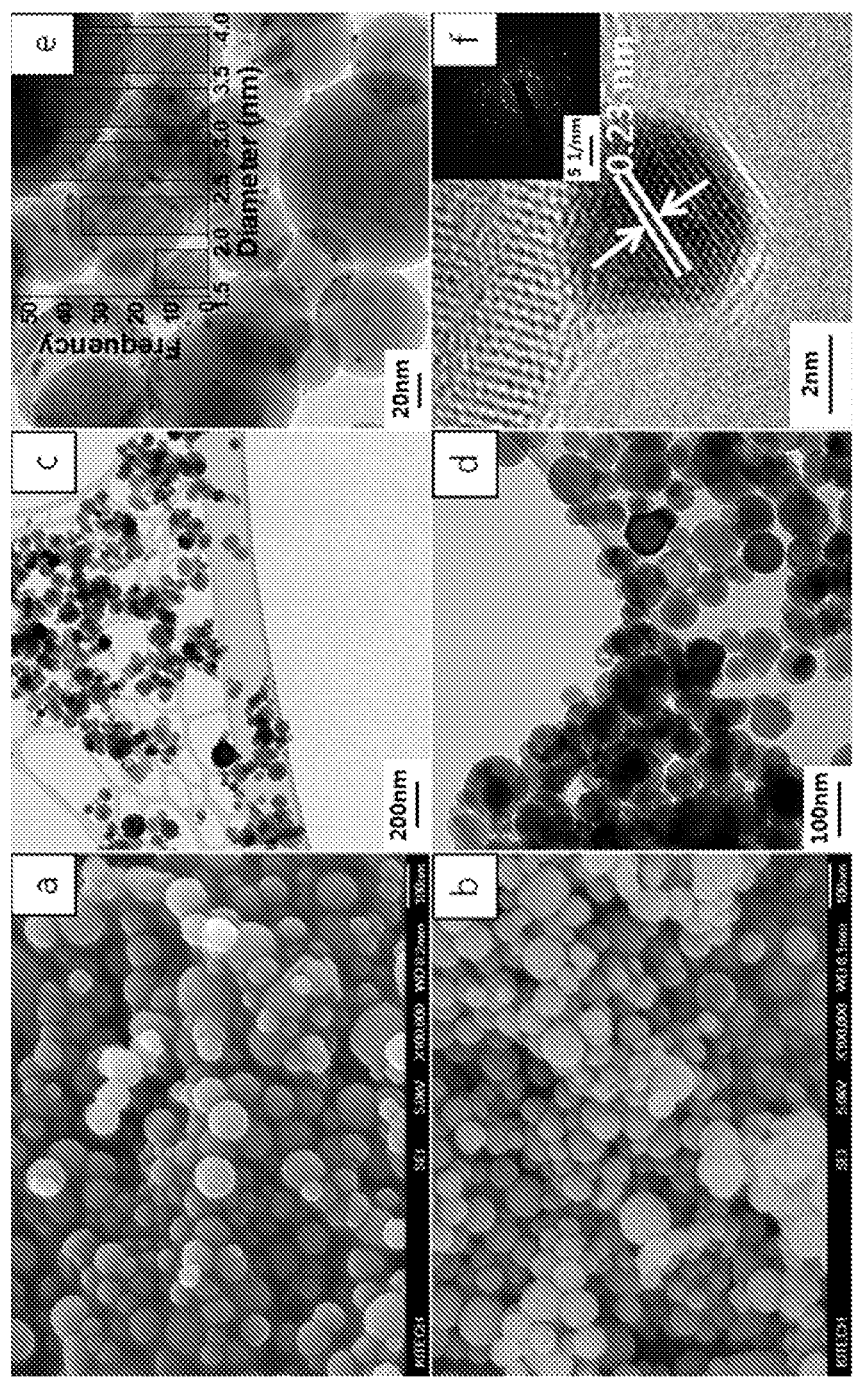
FIGS. 2a and b are scanning electron microscope (SEM) images of HAP and an Au/HAP-supported catalyst of Preparation Example 1 of the present invention, respectively, c, d, and e are transmission electron microscope (TEM) images of Preparation Example 1, in which the bar graph of e illustrates the size distribution of Preparation Example 1, and f shows a high-resolution TEM (HR-TEM) image of Preparation Example 1, in which the introduced image illustrates an SAED pattern of gold nanoparticles.

FIG. 2 shows the electron microscope images. With reference to FIG. 2, a and b are SEM images of HAP and the Au/HAP-supported catalyst of Preparation Example 1 of the present invention, respectively, c, d, and e are TEM images of Preparation Example 1, in which the bar graph of e illustrates the size distribution of Preparation Example 1, and f shows the HR-TEM image of Preparation Example 1, in which the introduced image illustrates the SAED pattern of gold nanoparticles.

With reference to FIGS. 2a and b, it can be seen that the morphology of HAP remains very steady during the deposition of Au after Au loading. Also, with reference to FIGS. 2c, d, e and f, the TEM and HR-TEM images of the Au/HAP nanocatalyst demonstrated the presence of Au nanoparticles having a size of 1.0 to 4.0 nm. With reference to the bar graph of FIG. 2e, the size distribution of Au nanoparticles was shown to mostly fall in the range of 2.0 to 4.0 nm. With reference to FIG. 2f, the d-spacing of 0.23 nm measured in the HR-TEM image corresponded to the [111] lattice plane of the Au nanoparticles, and matched the values reported in the literature. The upper right SAED pattern introduced in FIG. 2f showed the presence of highly crystalline dots confirming the formation of the Au/HAP nanocatalyst.

Figure 3:
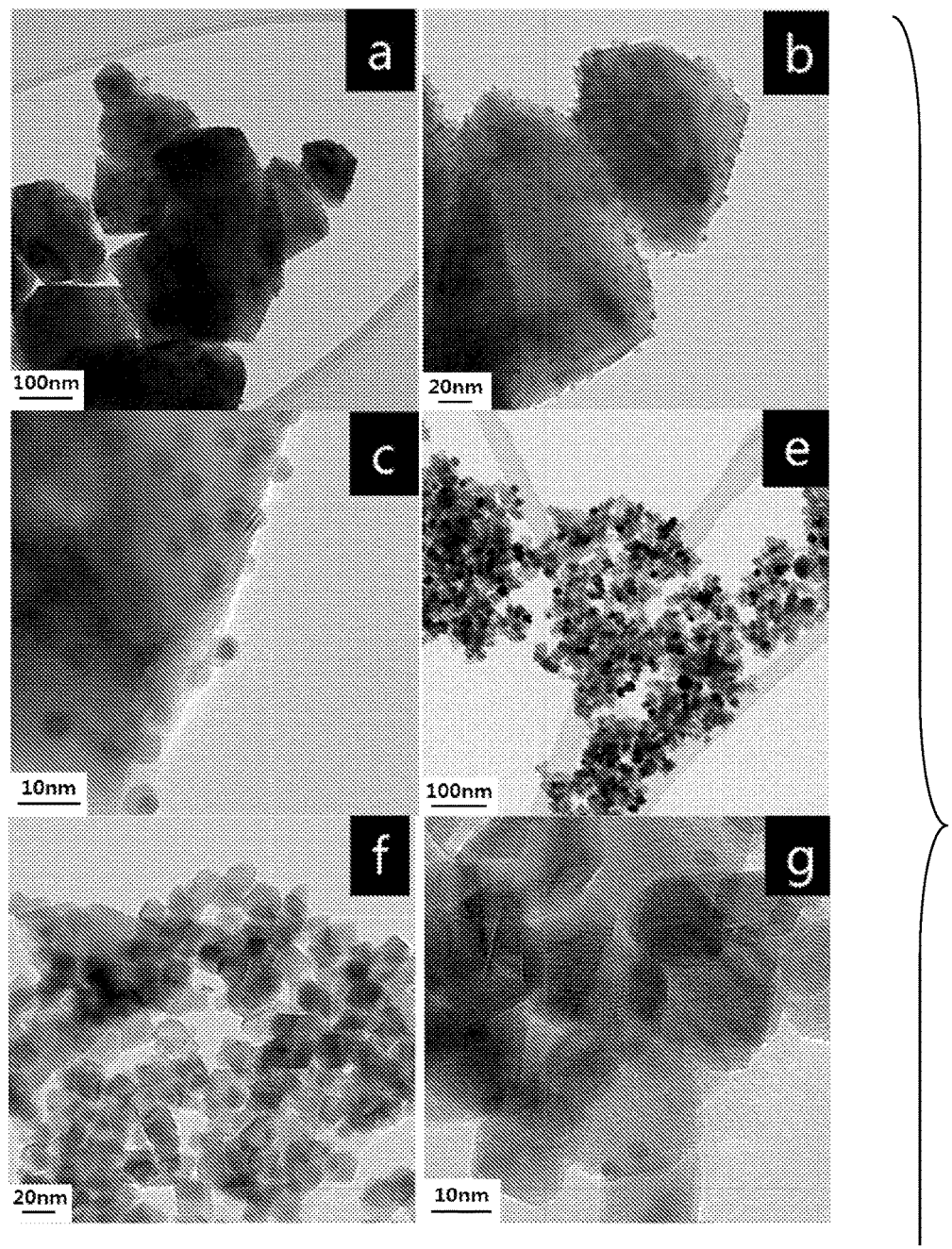
FIGS. 3(a), (b) and (c) are TEM images of Au/ZrO$_2$ of Comparative Preparation Example 3, (e), (f) and (g) are TEM images of Au/CeO$_2$ of Comparative Preparation Example 5, and (h), (i) and (j) are TEM images of Au/TiO$_2$ of Comparative Preparation Example 4.
Figure 3:
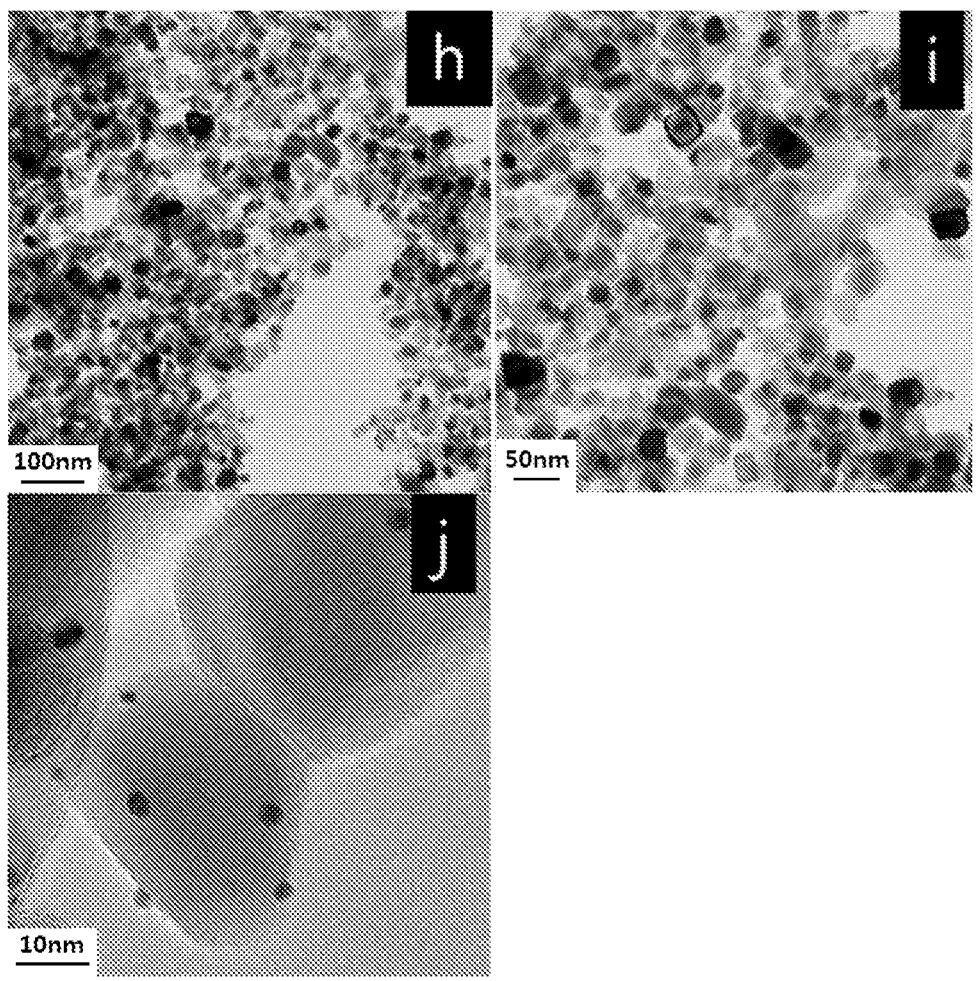

In FIG. 3, (a), (b) and (c) are TEM images of $Au/ZrO_2$, (e), (f) and (g) are TEM images of $Au/CeO_2$, and (h), (i) and (j) are TEM images of $Au/TiO_2$. In FIG. 3, the support and the gold nanoparticles supported on the support can be confirmed.

Figure 4:
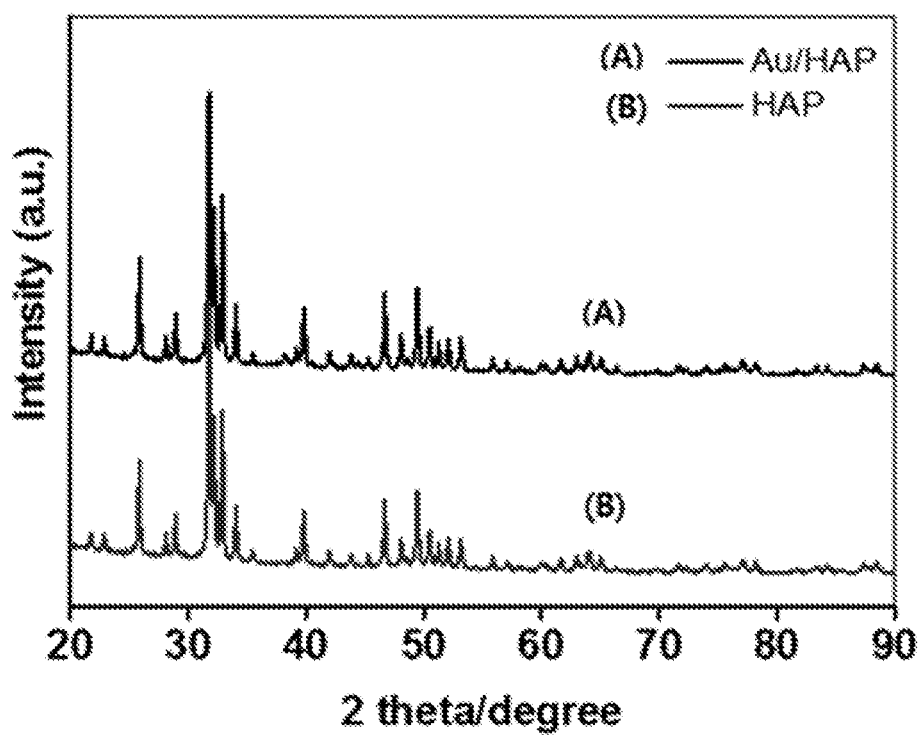
FIG. 4 shows the results of XRD of HAP and Preparation Example 1.

FIG. 4 shows the results of XRD of HAP and Preparation Example 1. With reference to FIG. 4, the crystallinity of the HAP and Au/HAP nanocatalyst of Preparation Example 1 was confirmed through XRD. The XRD pattern of HAP was very similar to that of the Au/HAP nanocatalyst, indicating that there was no change in the crystallinity of HAP even after Au loading.

Figure 5:
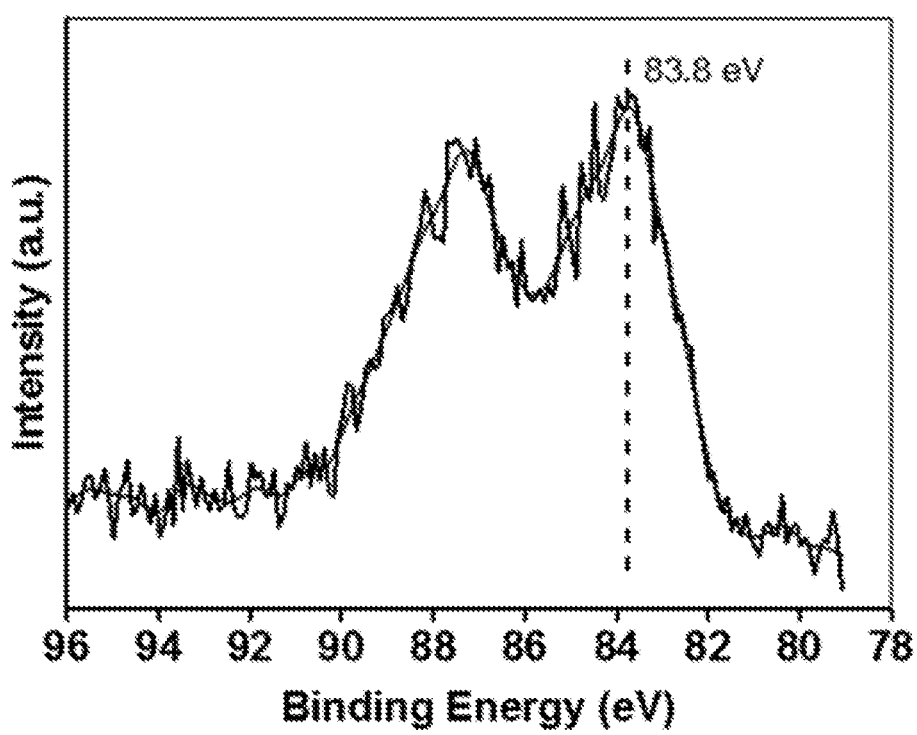
FIG. 5 shows the results of X-ray photoelectron spectroscopy of Preparation Example 1.

FIG. 5 shows the results of X-ray photoelectron spectroscopy of Preparation Example 1. With reference to FIG. 5, the valence state of Au in the Au/HAP nanocatalyst was assayed through X-ray photoelectron spectroscopy (XPS), and the spectrum (Au4f region of 78 to 96 eV) of the Au/HAP nanocatalyst was shown. Actually, the characteristic peak at (83.8±0.1) eV is due to the presence of gold nanoparticles. Based on the results thus obtained, the typical binding energy values of the metallic Au nanoparticles were consistent with the Au-based catalyst reported in the literature.

Figure 6:
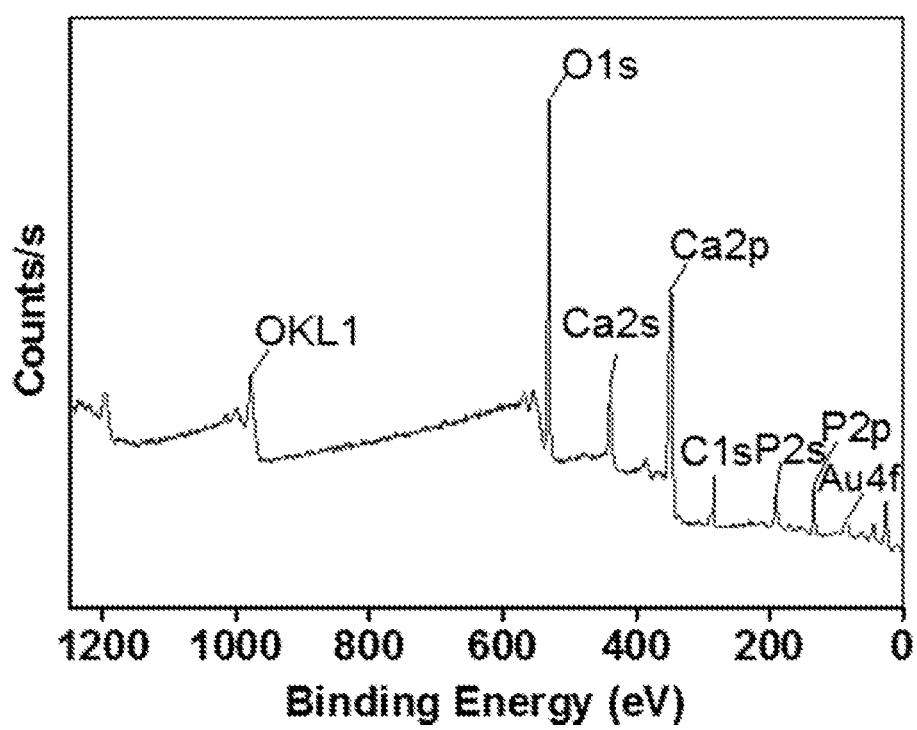
FIG. 6 shows the XPS spectrum of Preparation Example 1.

FIG. 6 shows the XPS spectrum of Preparation Example 1. With reference to FIG. 6, the presence of all the elements (Ca, P, O) including the Au element is clearly shown. In the XPS spectrum analysis, an additional peak of C 1s at 284.6 eV was generated from the residual carbon used as a standard reference.

Analysis of Reaction Mechanism

Figure 7:
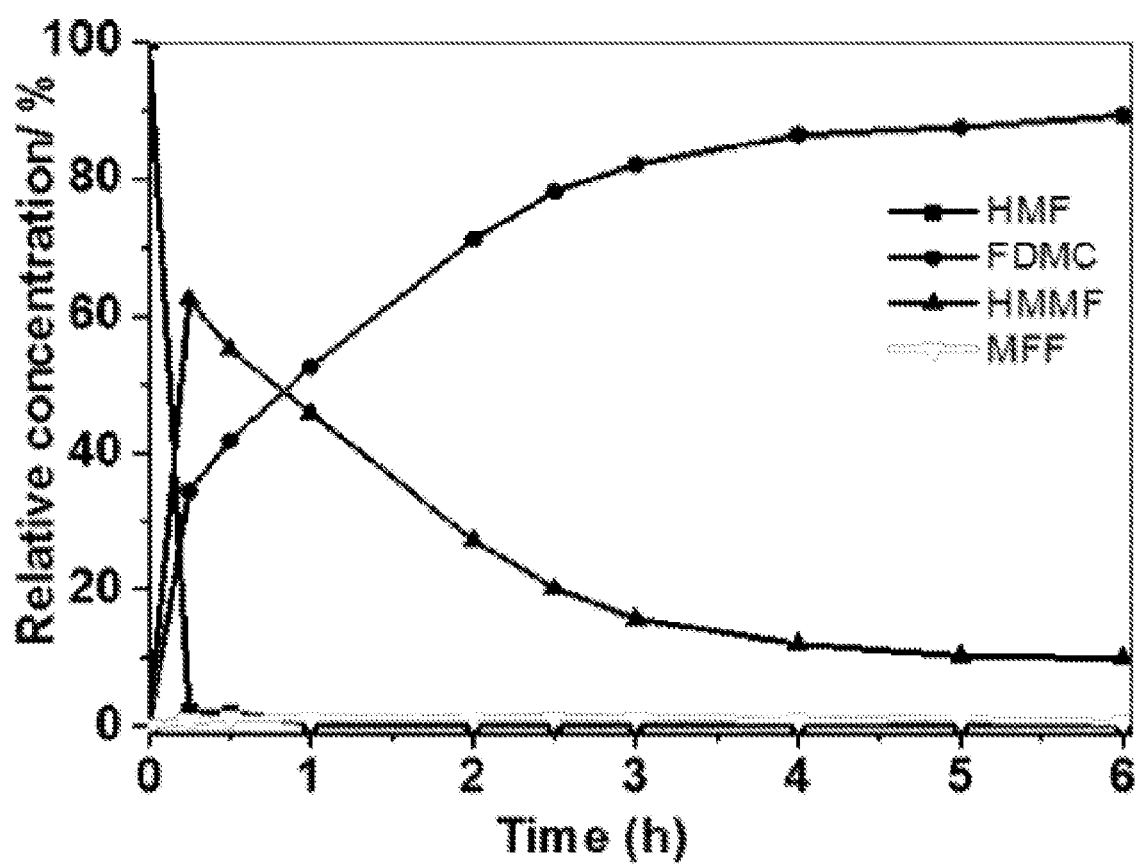
FIG. 7 is a graph showing the results of oxidative esterification of HMF into FDMC over time for 1 to 6 hr in Example 1.

FIG. 7 is a graph showing the results of oxidative esterification of HMF into FDMC over time for 1 to 6 hr in Example 1.

With reference to FIG. 7, based on the results of monitoring the reaction progression over time, it was observed that HMF was rapidly converted into 5-hydroxymethyl methyl furoate (HMMF) in a short reaction time in the initial stage. As the time increased further, it was observed that the intermediate HMMF was gradually converted into methyl 5-formyl-2-furoate (MFF) at a slow rate. Furthermore, MMF, as another intermediate formed from HMMF, was converted into FDMC at a higher rate. Therefore, as shown in FIG. 7, it was confirmed that the oxidative esterification of HMF proceeds through a series of reactions in which the aldehyde group of HMF can be oxidized faster than the alcohol group.

Analysis of Product

Figure 8A:
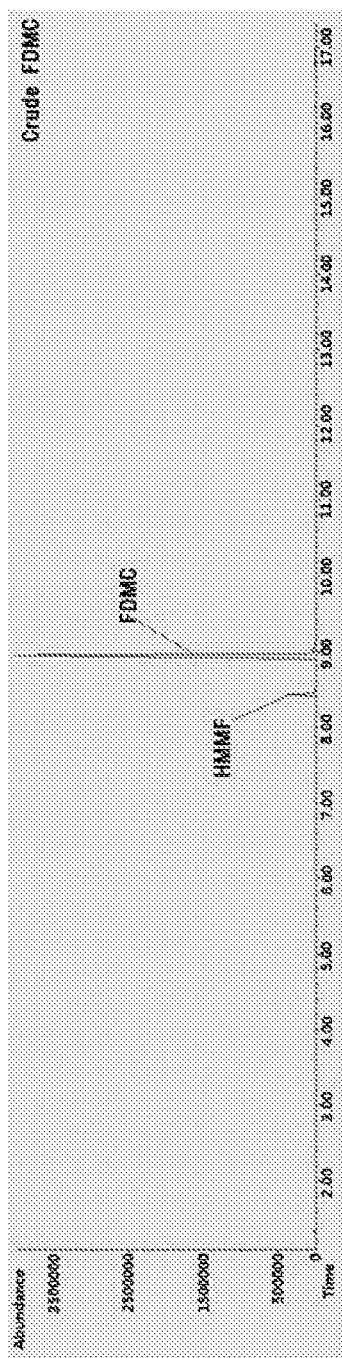
FIG. 8A shows a GC-MS graph of the crude product mixture obtained through oxidative esterification of HMF of Example 1.
Figure 8B:
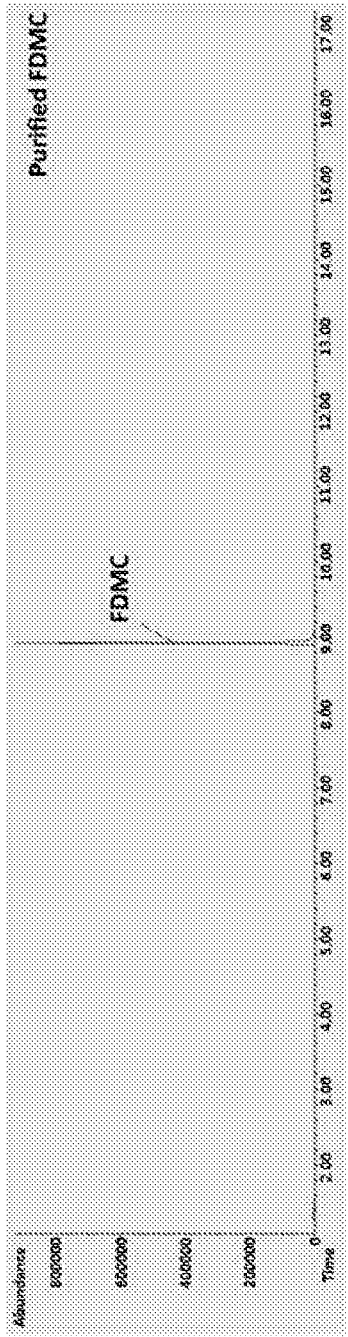
FIG. 8B shows a GC-MS graph of pure FDMC obtained from the crude product mixture of Example 1.
Figure 9:
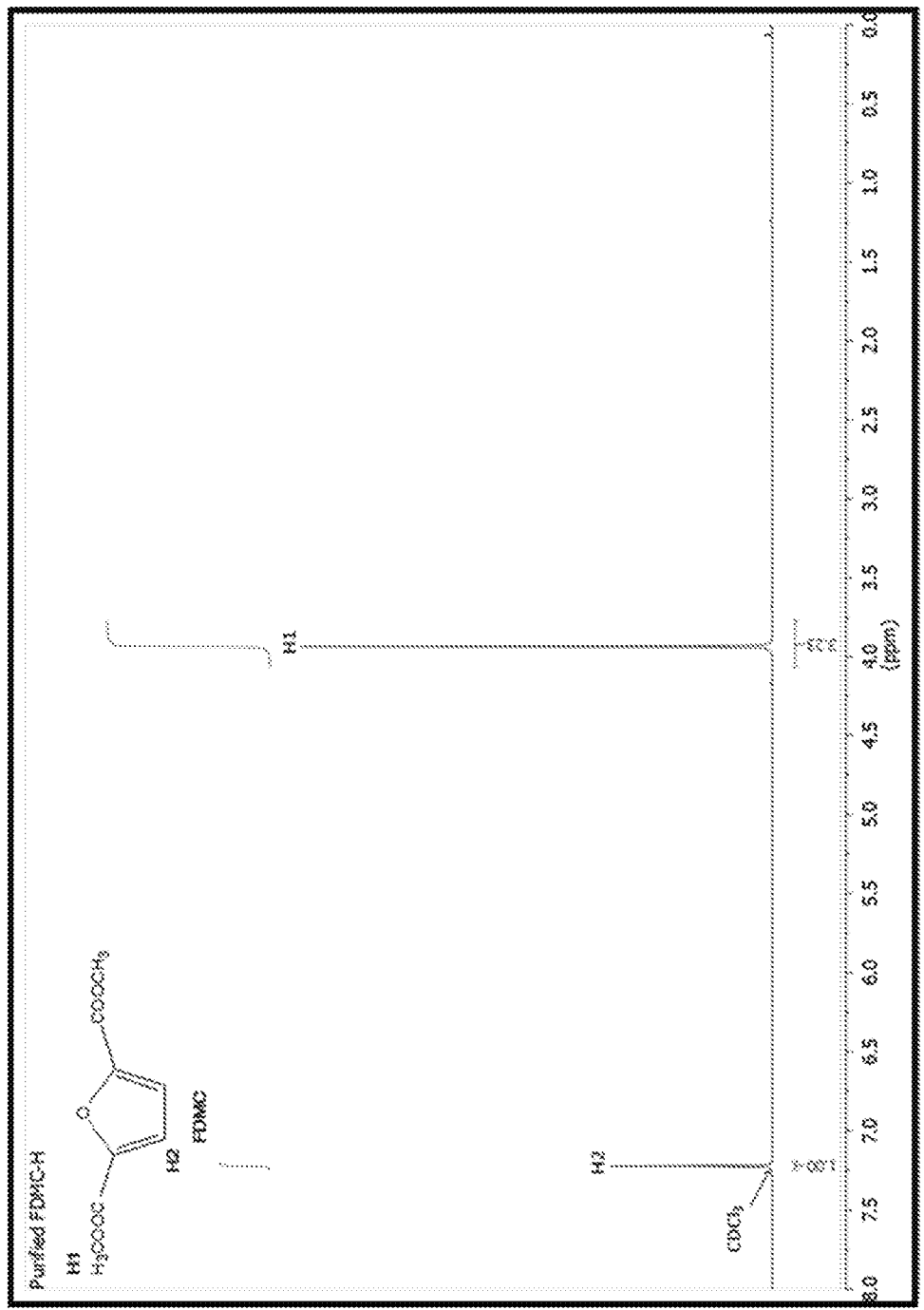
FIGS. 9 to 12 show the $^1$H-NMR spectrum of FDMC, $^1$H-NMR spectrum of HMMF, $^{13}$C-NMR spectrum of FDMC, and $^{13}$C-NMR spectrum of HMMF, respectively.
Figure 10:
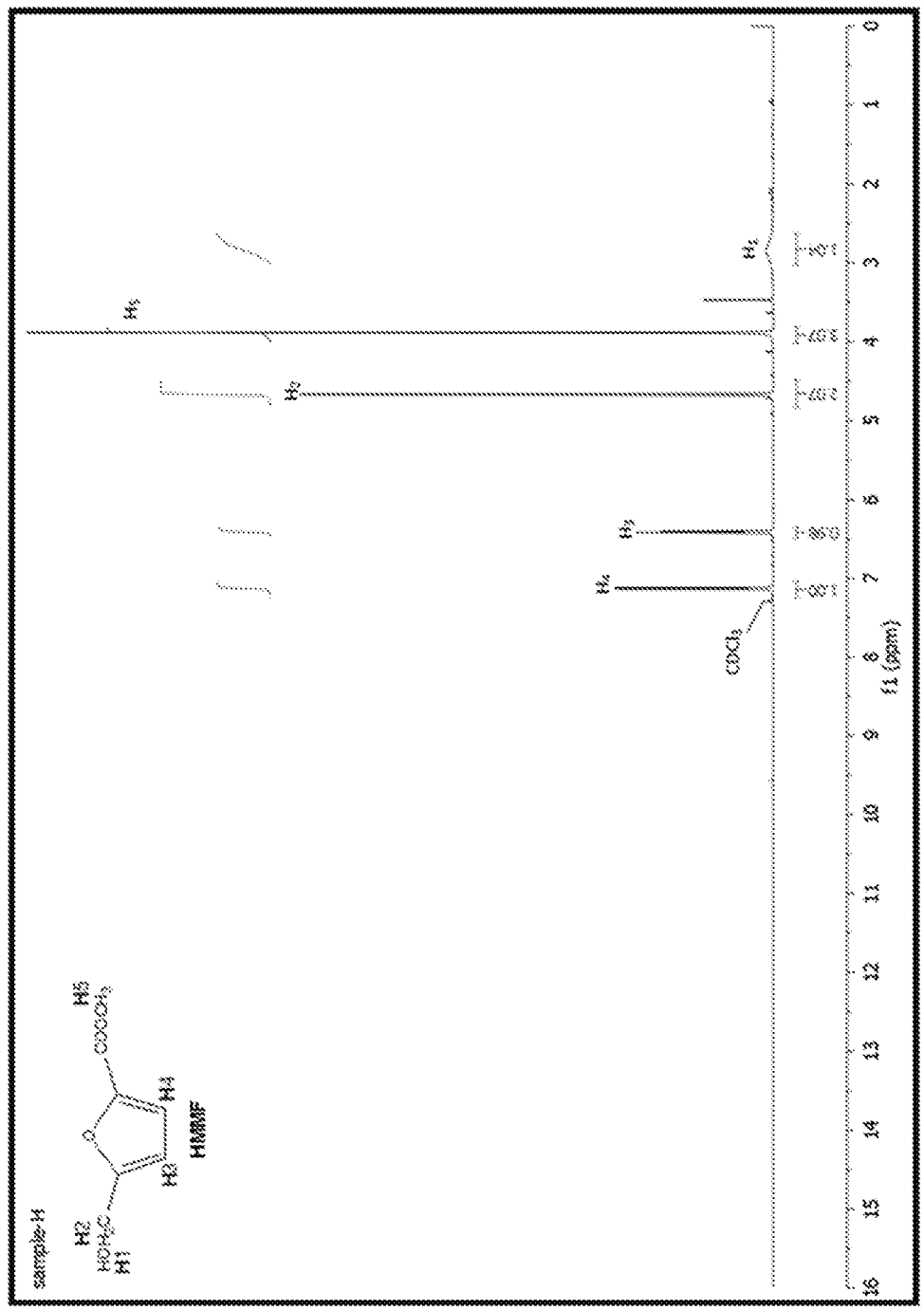
Figure 11:
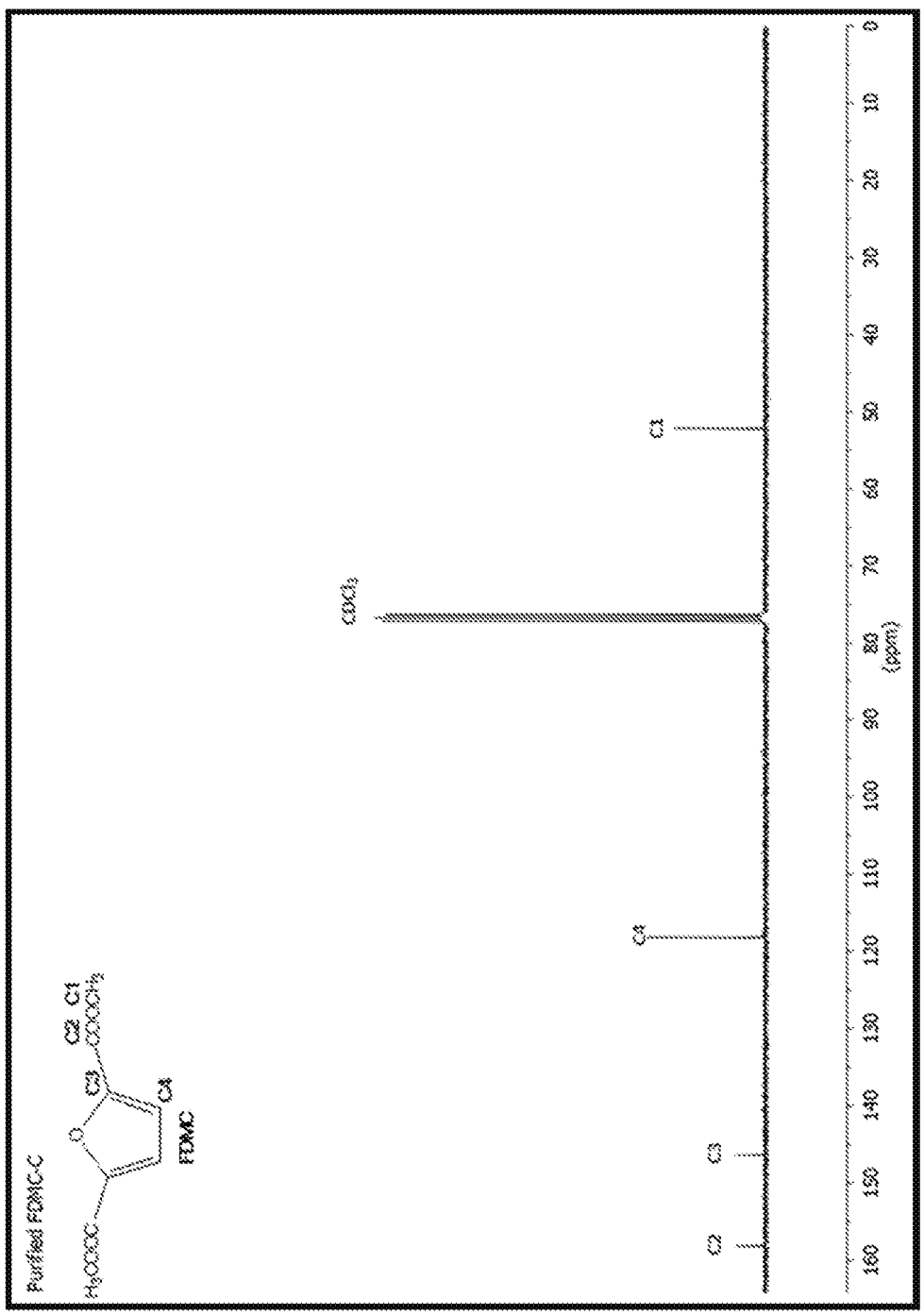
Figure 12:
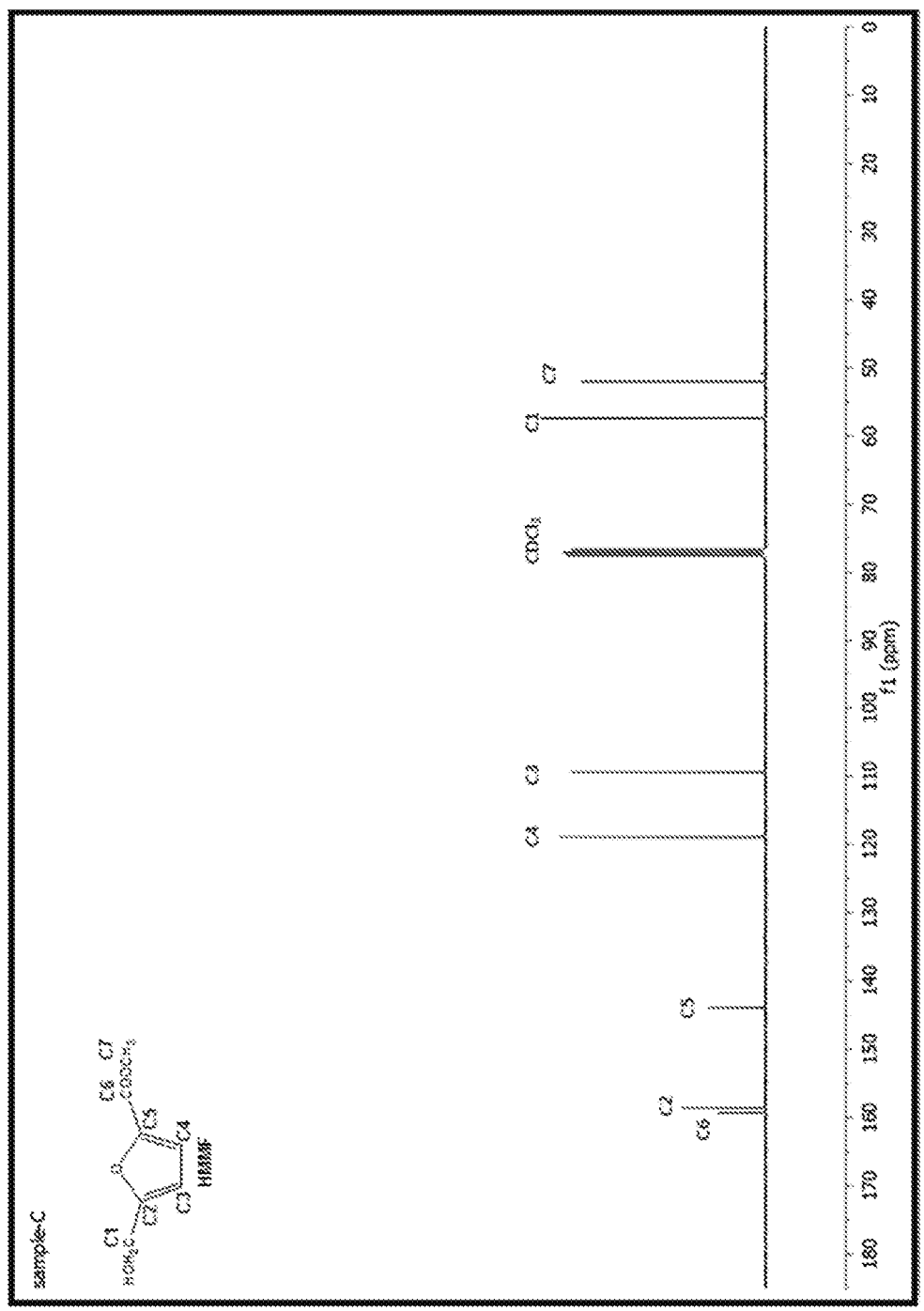

FIG. 8(a) shows a GC-MS graph of the crude product mixture obtained through oxidative esterification of HMF of Example 1, and (b) shows a GC-MS graph of pure FDMC obtained from the crude product mixture of Example 1. With reference to FIG. 8, the crude product mixture showed a large amount of FDMC having a small amount of HMMF as an intermediate.

FIGS. 9 to 12 show the $^1$H-NMR spectrum of FDMC, $^1$H-NMR spectrum of HMMF, $^{13}$C-NMR spectrum of FDMC, and $^{13}$C-NMR spectrum of HMMF, respectively.

In the mixture of hexane and methanol at 3:1, after crystallization of the crude FDMC, pure FDMC was obtained. FDMC was purified through a crystallization process. After the production reaction, methanol was evaporated from the product mixture using a rotary evaporator until a saturated solution resulted. Then, hexane was added (in an amount at least 3 times the amount of methanol) and the resulting mixture was allowed to stand for 24 hr so as to crystallize. The solid crystals were observed, separated by filtration, and dried under reduced pressure. FDMC (solid) and HMMF (yellow semi-liquid) were obtained, and the materials thus obtained can be confirmed to be FDMC and HMMF through FIGS. 9 to 12.

Analysis of Conversion Rate, Yield and Selectivity: HPLC

Through HPLC (Agilent Technologies 1200 series, Bio-Rad Aminex HPX-87 H pre-packed column, and UV-detector), the conversion rate (C), the production yield (Y), and the selectivity (S) were calculated as follows, and the conversion rate, yield and selectivity were compared depending on the kind of support of the catalyst.

Effect of Temperature

The effect of temperature on the oxidative esterification of HMF into FDMC was measured, and the results are shown in Table 3 below. Elevating the temperature from 110° C. to 130° C. had a positive effect on the HMF conversion rate and the FDMC yield. A 100% conversion rate of HMF was achieved at a high temperature of 150° C., but the FDMC yield decreased from 89.3% to 20.9% as a result of methanol oxidation of carbon dioxide or methyl formate (MF) to the corresponding product.

Effect of Air Pressure

The effect of air pressure on the oxidative esterification of HMF into FDMC was measured, and the results are shown in Table 3 below. In order to evaluate the effect of air pressure, the oxidation of HMF was performed at a constant temperature of 130° C. under the condition in which the air pressure was varied from 1.7 MPa to 3.1 MPa. At an air pressure of 1.7 MPa, the HMF conversion rate was 99.0% but the FDMC yield was as low as 61.0%. After the reaction, two intermediates, namely HMMF and MFF, were found. When the pressure was increased from 1.7 to 2.4 MPa (entry 4 and 5), the FDMC yield reached to 89.3% from 61.0%, indicative of a strong effect of air pressure. Meanwhile, even when the air pressure was further increased, there was no great effect on the FDMC yield.

TABLE 3

| | Reaction temperature (° C.)/Reaction air pressure (MPa) | $C_{HMF}$ (%) | $Y_{FDMC}$ (%) | $Y_{HMMF}$ (%) | $Y_{MMF}$ (%) |
|---|---|---|---|---|---|
| Example 1 | 130/2.4 | 99.9 | 89.3 | 10.0 | 0.7 |
| Example 2 | 110/2.4 | 99.0 | 51.8 | 42.2 | 6.0 |
| Example 3 | 150/2.4 | 100 | 20.9 | 15.9 | 0.9 |
| Example 4 | 130/1.7 | 99.0 | 61.0 | 38.1 | 0.9 |
| Example 5 | 130/3.1 | 100 | 89.6 | 9.6 | 0.8 |

Effects of Support and Metal

Table 4 below shows the results of comparison of the conversion rate, yield and selectivity depending on the kind of support or metal of the catalyst when FDMC is prepared through HMF oxidation in the presence of air.

TABLE 4

| | Catalyst | HMF/Metal (mol ratio) | $C_{HMF}$, % | $Y_{FDMC}$, % | $Y_{HMMF}$, % | $Y_{NI}$, % |
|---|---|---|---|---|---|---|
| Example 1 | Au/HAP | 100 | 99.9 | 89.3 | 10.0 | 0.6 |
| Comparative Example 1 | Pd/HAP | 100 | 26.6 | 0.0 | 9.0 | — |
| Comparative Example 2 | Ru/HAP | 100 | 68.2 | 0.0 | 0.0 | — |
| Comparative Example 3 | Au/ZrO$_2$ | 100 | 99.3 | 80.9 | 18.1 | 0.0 |
| Comparative Example 4 | Au/TiO$_2$ | 100 | 98.9 | 36.1 | 26.5 | 28.6 |
| Comparative Example 5 | Au/CeO$_2$ | 100 | 80.9 | 21.9 | 29.5 | 32.2 |
| Comparative Example 6 | Au/MgAl$_2$O$_4$ | 93.4 | 78.2 | 42.8 | 14.6 | 12.5 |
| Comparative Example 7 | Au/MnCo$_2$O$_4$ | 93.4 | 74.3 | 0.0 | — | 20.0 |
| Comparative Example 8 | HAP | — | 9.5 | — | — | — |

HMMF = 5-hydroxymethyl methyl furoate (monoester)
NI: Not identified

The "HMF conversion rate" is the value, expressed as a percentage, obtained by dividing the number of moles of HMF that reacted by the number of moles of HMF that were used. The "FDMC yield" is the value, expressed as a percentage, obtained by dividing the number of moles of FDMC actually produced by the number of moles of FDMC theoretically produced. The "FDMC selectivity" is the value, expressed as a percentage, obtained by dividing the FDMC yield by the HMF conversion rate.

In Tables 3, 4 and 5 below, C designates the conversion rate, Y designates the yield, and S designates the selectivity.

The FDMC yield was calculated based on the HMF conversion rate and confirmed through calibration of the standard product and reactant solutions.

As is apparent from Table 4, when hydroxyapatite (HAP) of Example 1 was used as the support of the gold-nanoparticle-supported catalyst, the HMF conversion rate and the FDMC yield were the highest, namely 99.9% and 89.3%, respectively, compared to when using the supports of Comparative Examples.

Also, the catalysts using metals different from gold, as in Comparative Example 1 using palladium and Comparative Example 2 using ruthenium, exhibited an extremely low FDMC yield of 0%. Although not shown in Table 4, DFF, not FDMC, was obtained at yields of 16.7% and 66.7% using the Pd/HAP of Comparative Example 1 and the Ru/HAP of Comparative Example 2, respectively.

In Comparative Example 3 using Au/ZrO$_2$, which is known as a good oxidation catalyst, the oxidative esterification of HMF into FDMC was performed under the same conditions. The Au/ZrO$_2$ of Comparative Example 3 exhibited a good FDMC yield of 80.9%, and the monoester HMMF yield of 18.1%, separately from FDMC.

In Comparative Example 4 using the Au/TiO$_2$ catalyst, FDMC was obtained at a yield of 36.1%, indicative of poor activity, and the Au/CeO$_2$ of Comparative Example 5 exhibited a byproduct yield of 28.6%, a monoester HMMF yield of 29.5% and an FDMC yield of 21.9%. In Comparative Example 6 using Au/MgAl$_2$O$_4$ as the gold catalyst supported on a MgAl$_2$O$_4$ spinel, an FDMC yield of 42.8%, a monoester HMMF yield of 14.6% and a byproduct yield of 12.5% were exhibited. In Comparative Example 7 using Au/MnCo$_2$O$_4$ as the gold catalyst supported on MnCo$_2$O$_4$, although not shown in Table 5, DFF was obtained as the main product at a yield of 54.0%. The low activity of Au/MnCo$_2$O$_4$ to with FDMC is deemed to be due to the acidic properties of the Bronsted and Lewis acid of the support, i.e. MnCo$_2$O$_4$. In Comparative Example 8, HAP alone seldom caused HMF oxidation.

Effect of Oxygen Atmosphere Pressure

Table 5 below shows the results of comparison of the yield and selectivity depending on the kind of support of the catalyst when FDMC is prepared through an oxidation reaction of HMF without the use of a base additive under oxygen.

As is apparent from Table 5, although it is difficult to produce FDMC on a large scale because of high explosivity upon conventional oxidation using a pure oxygen oxidizing agent, when comparing Example 7, obtained through the reaction under air pressure, with Example 9, obtained through the reaction under oxygen pressure using the same HAP support, Example 7 under air pressure exhibited a higher HMF conversion rate, FDMC yield and FDMC selectivity, namely 99.9%, 88.7% and 88.8% respectively. Therefore, it was confirmed that FDCA can be produced on a large scale because of obtaining FDMC through an oxidation reaction in air, which is not readily explosive.

TABLE 5

| | HMF/Au (mol ratio) | $C_{HMF}$ (%) | $Y_{FDMC}$ (%) | $S_{FDMC}$ (%) |
|---|---|---|---|---|
| Example 7 | 93.4 | 99.9 | 88.7 | 88.8 |
| Example 9 | 93.4 | 99.9 | 86.3 | 86.4 |

HMMF: 5-hydroxymethyl methyl furoate

Effect of Gold of Supported Catalyst/HMF Mol Ratio

Table 6 below shows the results of comparison of the yield and selectivity depending on the content ratio of gold (Au) nanoparticle catalyst and HMF when FDMC is prepared through oxidative esterification of HMF in the air.

TABLE 6

| | HMF/Au (mol ratio) | $C_{HMF}$ (%) | $Y_{FDMC}$ (%) | $S_{FDMC}$ (%) | $Y_{HMMF}$ (%) |
|---|---|---|---|---|---|
| Example 6 | 100 | 99.6 | 86.7 | 87.1 | 13.3 |
| Example 7 | 93.4 | 99.9 | 88.7 | 88.8 | 11.2 |
| Example 8 | 62.5 | 99.9 | 89.6 | 90.3 | 10.4 |

HMMF: 5-hydroxymethyl methyl furoate

As is apparent from Table 6, when the amount of the catalyst was increased, the FDMC yield was raised. At the ratio (HMF/Au=100), the FDMC yield was a maximum of 86.7%, and at the ratio (HMF/Au=62.5), the FDMC yield was a maximum of 89.6%.

Therefore, based on the yield and selectivity depending on the content ratio of gold (Au) nanoparticle catalyst and HMF, it can be confirmed that the FDMC yield increases with an increase in the content ratio of gold nanoparticle catalyst.

Analysis of Recycling of Catalyst

Figure 13:
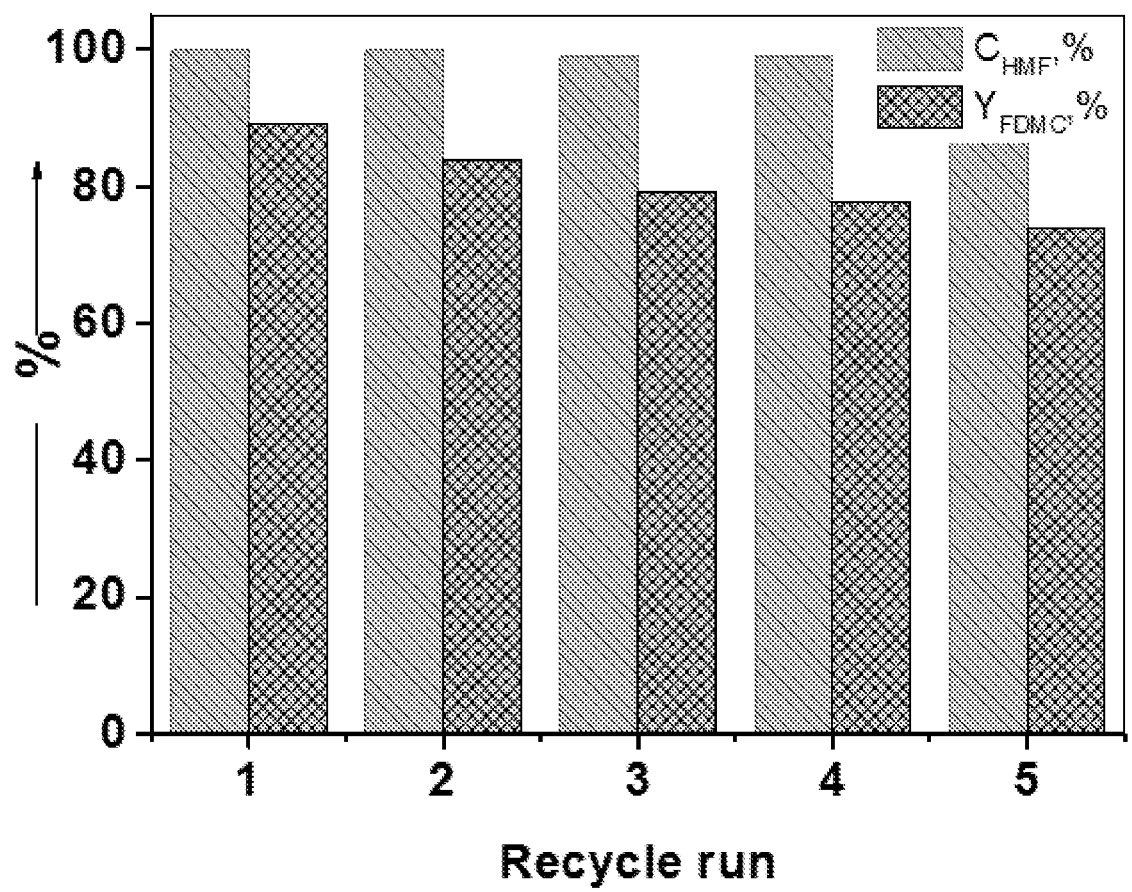
FIG. 13 is a graph showing the HMF conversion rate and the FDMC yield upon recycling of the Au/HAP nanocatalyst of Preparation Example 1.

FIG. 13 is a graph showing the HMF conversion rate and the FDMC yield upon recycling of the Au/HAP nanocatalyst of Preparation Example 1. After the reaction, the catalyst was separated from the product mixture through centrifugation in order to minimize the loss of catalyst weight. The recovered catalyst was thoroughly washed with methanol, dried in a vacuum oven at 45° C. for 6 hr and then recycled. The HMF/Au ratio was always kept constant at 100.

With reference to FIG. 13, the Au/HAP nanocatalyst exhibited significant activity even after 5 consecutive cycles without loss of activity compared to the initial state. The results thus obtained showed that the Au/HAP nanocatalyst is quite stable under the applied reaction conditions. Au/HAP was concluded to be a very strong heterogeneous catalyst for the oxidation esterification of HMF to synthesize FDMC.

According to embodiments of the present invention, 2,5-furandimethylcarboxylate (FDMC) is simply produced through a safe process without the use of an explosive oxidizing agent, unlike conventional methods of preparing 2,5-furandimethylcarboxylate (FDMC). Furthermore, the preparation of FDMC through preparing FDCA and then performing esterification thereof with an alcohol is a two-step process, but the present invention is effective in directly preparing FDMC from HMF through oxidative esterification in a single step.

According to the present invention, air and an alcohol are used as a reactant and a solvent, thus exhibiting improved safety and convenience compared to when conventional solvents are used.

Although the conventional preparation of 2,5-furandicarboxylic acid (FDCA) is problematic in that 2,5-furandicarboxylic acid (FDCA) has low solubility in an industrial solvent, the present invention is capable of effectively solving the problem of low solubility due to the use of 2,5-furandimethylcarboxylate (FDMC).

According to the present invention, 2,5-furandimethylcarboxylate (FDMC) can be effectively prepared at high selectivity and high yield using an HAP support, rather than other supports, through reaction in a single vessel under high pressure in the presence of an Au/HAP catalyst.

Although the embodiments of the present invention have been disclosed for illustrative purposes, those skilled in the art will appreciate that the present invention may be embodied in other specific forms without changing the technical spirit or essential features thereof. Thus, the embodiments described above should be understood to be non-limiting and illustrative in every way. For example, respective elements described as having an integrated form may be discretely used, and discrete elements may be used in the state of being combined.

The scope of the present invention is defined by the claims, which will be set forth below, rather than by the above detailed description, and all variations or modifications deducible from the meanings, scope and equivalents of the claims are intended to be included in the scope of the present invention.

INDUSTRIAL APPLICABILITY

According to embodiments of the present invention, 2,5-furandimethylcarboxylate (FDMC) is simply produced through a safe process without the use of an explosive oxidizing agent (pure oxygen), unlike conventional methods of preparing 2,5-furandimethylcarboxylate (FDMC). Furthermore, the preparation of FDMC through preparing FDCA and then performing esterification thereof with an alcohol is a two-step process, but the present invention is effective in directly preparing FDMC from HMF through oxidative esterification in a single step.

According to the present invention, air and an alcohol are used as a reactant and a solvent, thus improving safety and convenience compared to when conventional solvents are used.

Although the conventional preparation of 2,5-furandicarboxylic acid (FDCA) is problematic in that 2,5-furandicarboxylic acid (FDCA) has low solubility in an industrial solvent, the present invention is capable of effectively solving the problem of low solubility due to the use of 2,5-furandimethylcarboxylate (FDMC).

According to the present invention, 2,5-furandimethylcarboxylate (FDMC) can be effectively prepared at high selectivity and high yield using an HAP support, rather than other supports, through reaction in a single vessel under high pressure in the presence of an Au/HAP catalyst.

The invention claimed is:

1. A method of preparing 2,5-furandimethylcarboxylate (FDMC), comprising:
    preparing 2,5-furandimethylcarboxylate (FDMC) by subjecting a reaction mixture comprising 5-hydroxymethylfurfural (HMF), air and an alcohol solvent to oxidative esterification using a gold (Au)-nanoparticles/hydroxyapatite (HAP)-supported catalyst,
    wherein the HAP is used as a support on which the gold (Au) nanoparticles are supported,
    wherein the oxidative esterification is carried out by entering air and maintaining an air pressure of 1.7 to 3.1 MPa.

2. The method of claim 1, wherein an amount of the gold (Au) nanoparticles is 0.5 wt % to 10 wt % based on 100 wt % of the gold-nanoparticles/HAP-supported catalyst.

3. The method of claim 1, wherein a gold content of the HAP supported catalyst is 0.5 mol to 2.0 mol based on 100 mol of the hydroxymethylfurfural (HMF).

4. The method of claim 1, wherein the alcohol solvent is methanol.

5. The method of claim 1, wherein the oxidative esterification is carried out at a temperature of 110° C. to 150° C. for 3 hr to 12 hr.

* * * * *